(12) United States Patent
Carson et al.

(10) Patent No.: US 6,461,379 B1
(45) Date of Patent: Oct. 8, 2002

(54) LOCALIZED BODILY COOLING/HEATING APPARATUS AND METHOD

(75) Inventors: Gary A. Carson, Golden, CO (US); Marc Voorhees, Arvada, CO (US)

(73) Assignee: MediVance, Incorporated, Louisville, CO (US)

( * ) Notice: Subject to any disclaimer, the term of this patent is extended or adjusted under 35 U.S.C. 154(b) by 17 days.

(21) Appl. No.: 09/845,843

(22) Filed: Apr. 30, 2001

(51) Int. Cl.[7] ................................................. A61F 7/00
(52) U.S. Cl. ........................ 607/104; 607/108; 607/112
(58) Field of Search ................................ 607/104, 107, 607/108–112, 114; 105/46; 219/211, 528

(56) References Cited

U.S. PATENT DOCUMENTS

| 998,804 A | 7/1911 | Salisbury |
|---|---|---|
| 2,043,721 A | 6/1936 | Warwick |
| 2,224,876 A | 12/1940 | Matys |
| 2,416,788 A | 3/1947 | Andrews |
| 2,566,600 A | 9/1951 | Colon |
| 3,587,577 A | 6/1971 | Smirnov et al. |
| 4,074,369 A | 2/1978 | Harmon |
| 4,987,618 A | 1/1991 | Tolbert |
| 5,235,709 A | 8/1993 | Terlep |
| D347,491 S | 5/1994 | Holloway |
| 5,342,411 A | 8/1994 | Maxted et al. |
| 5,496,357 A * | 3/1996 | Jensen et al. ................ 607/108 |
| 5,871,526 A * | 2/1999 | Gibbs et al. .................... 165/46 |
| 6,109,338 A * | 8/2000 | Butzer ........................... 165/46 |
| 6,197,045 B1 * | 3/2001 | Carson ......................... 601/148 |
| 6,210,427 B1 * | 4/2001 | Augustine et al. .............. 5/421 |
| 6,238,427 B1 * | 5/2001 | Matta .......................... 607/104 |
| 6,276,155 B2 * | 8/2001 | Siman-Tov et al. ............ 165/46 |
| 6,352,550 B1 * | 3/2002 | Gildersleeve et al. ........ 607/108 |

* cited by examiner

*Primary Examiner*—Roy D. Gibson
(74) *Attorney, Agent, or Firm*—Marsh Fischmann & Breyfogle LLP (57) ABSTRACT

The present invention provides for rapid heat transfer with a tissue region of interest (24) by the direct contact of a circulated thermal exchange fluid with the tissue region of interest (24). The tissue region of interest is covered with an appropriately configured flexible membrane (28). A spacing structure maintains a spaced relation between an interior side (30) of the flexible membrane (28) and the tissue region of interest (24) to define a fluid circulation space (34) for fluid flow therebetween. Thermal exchange fluid is drawn into the fluid circulation space (34) though an inlet (60) in the flexible membrane and out of the fluid circulation space (34) through an outlet (64) in the flexible membrane (28) under negative or nearly negative gauge pressure. The fluid directly contacts the tissue region of interest (24), resulting in cooling/heating of the tissue region of interest (24).

47 Claims, 11 Drawing Sheets

LOCALIZED BODILY COOLING/HEATING APPARATUS AND METHOD

FIELD OF INVENTION

The present invention generally relates to a method and apparatus for heat transfer with a patient, and more particularly to a method and apparatus for cooling and/or heating a localized tissue region of interest on a patient.

BACKGROUND OF THE INVENTION

The use of heating/cooling devices in medial applications is well established. By way of example, bodily heating may be employed for hypothermia patients. Hypothermia may occur, for example, in patients undergoing surgical procedures. It has been shown that nearly seventy five percent of all patients who undergo surgical procedures develop hypothermia from factors including anesthesia, air conditioning of the operating room, and infusion of cold blood or I-V solutions. Studies show that by reducing hypothermia, patient outcome is improved and recovery is quicker.

Further, bodily cooling has been proposed for stroke patients to reduce potential brain damage due to ischemia. In this regard, studies show that cooling the brain 2–3° C. yields neuro-protection that might hasten recovery. Additionally, during vascular procedures requiring circulatory arrest, a common technique is to cool the patient's core via cardiovascular extracorporeal perfusion to less than 15° C. In order to maximize protection of major organs, including the brain and spine, peripheral cooling may be employed to prevent rewarming via heat conduction from surrounding tissues.

To date, self-contained thermal exchange pads and other devices have been used for cooling and/or heating of a patient. Fluids, such as water, are circulated between layers of the thermal exchange pad to cool or heat the patient. For example, fluids colder/hotter than the patient's body temperature may be circulated through the pad to absorb/release heat from/to the patient, thereby achieving cooling/heating. While such devices have proven effective for many applications, the present inventor has recognized that further improved results are achievable in certain applications.

SUMMARY OF THE INVENTION

Accordingly the present invention provides a method and apparatus for enhanced heat transfer with a localized tissue region of interest. The apparatus/method utilizes a membrane configured for covering a tissue region of interest and a spacing structure that maintains a spacing relation between an interior side of the flexible membrane and the tissue region of interest to define a fluid circulation space therebetween. Thermal exchange fluid may be drawn into the fluid circulation space through an inlet in the flexible membrane and out of the fluid circulation space through an outlet in the flexible membrane. In this regard, the fluid directly contacts the tissue region of interest. A related fluid circulation system includes a pump connected downstream from the fluid outlet and a fluid reservoir connected upstream from the fluid inlet. When operated, the pump draws thermal exchange fluid from the reservoir, into, and out of the fluid circulation space. Thermal energy is exchangeable between the tissue region of interest and the thermal exchange fluid circulated within the fluid circulation space to cool and/or warm the tissue region of interest.

The fluid may be circulated under negative or nearly negative gauge pressure which has several advantages. For example, the flexible membrane is not distended/expanded by the pressure of the circulated fluid and thereby fluid velocity over the tissue region of interest is maximized thus maximizing heat transfer. Circulating the fluid under negative or nearly negative gauge pressure also achieves inherent sealing at the edges of the flexible membrane as compared to a positive pressure situation. Further, direct contact of the fluid with the tissue region of interest also enhances heat transfer where the tissue region of interest is covered by hair (e.g. a person's head) as compared with a thermal exchange pad which contains the fluid and prevents direct contact of the fluid with the tissue region of interest.

According to one aspect of the present invention, an apparatus for local exchange of thermal energy with a tissue region of interest includes a flexible membrane having an interior side and an exterior side. The flexible membrane is configured for covering the tissue region of interest. The flexible membrane may be comprised of an elastic material, such as silicone rubber, natural rubber, an elastomer, a thermoplastic polyurethane or a latex material, to allow for stretching of the flexible membrane to facilitate positioning of the flexible membrane over a body element (e.g., over a patient's head). The apparatus also includes a spacing structure for maintaining the interior side of the flexible membrane in a spaced relation with the tissue region of interest to define a fluid circulation space therebetween. The apparatus further includes at least one fluid inlet and at least one fluid outlet communicating with the fluid circulation space. A thermal exchange fluid is circulatable through the fluid circulation space from the inlet to the outlet at or near a negative gauge pressure (i.e. pressure measured relative to ambient pressure). In this regard, the thermal exchange fluid may be circulated through the fluid circulation space at a gauge pressure ranging from slightly positive (e.g., about 0.1 psi) to substantially negative (e.g., about −10.0 psi).

The spacing structure may be comprised of one or more ribs, one or more studs, or a combination of both. The spacing structure may be integrally molded to the interior side of the flexible membrane and project from the interior side of the flexible membrane. However, the spacing structure may also be removably attached to the interior side of the flexible membrane or may even be a separate structure such as a net or the like that is disposable between the tissue region of interest and the interior side of the flexible membrane. The spacing structure may define a plurality of fluid flow paths from the fluid inlet to the fluid outlet. In this regard, the fluid flow paths are generally of equal length from the fluid inlet to the fluid outlet and inhibit the formation of boundary layers of stationary thermal exchange fluid that may reduce the overall efficiency of the apparatus.

The flexible membrane may also include a sealable edge. In one embodiment the sealable edge may comprise a strip, located on the periphery of the interior side of the flexible membrane that is free of any spacing structure (e.g. smooth). In another embodiment, the strip may include a plurality of elongated parallel ridges projecting from an interior side of the strip. In use, the ridges are forced into the periphery of the tissue region of interest such that portions between the ridges are approximately coplanar with the tissue region of interest. In another embodiment, the sealable edge may include an adhesive material disposed on the interior side of the strip. The adhesive aids in facilitating a tight seal between the sealable edge and the periphery of the tissue region of interest. In this regard, the adhesive on the seal should be comprised of a material having sufficient adhesive strength for holding the flexible membrane in place without having too great of an adhesive strength so as to cause tissue damage during removal. Generally, for best results, the sealable edge should be positioned next to a portion of the patient's skin that lacks substantial hair. The above-described embodiments of the sealable edge allow the sealable edge to grip the patient's skin, and thus help maintain the conformance of the flexible membrane to the tissue region of interest to limit unintentional movement of the flexible membrane.

According to another aspect of the present invention, a system for local exchange of thermal energy with a tissue region of interest includes a flexible membrane configured for covering the tissue region of interest and a spacing structure that maintains an interior side of the flexible membrane in a spaced relation with the tissue region of interest to define a fluid circulation space therebetween. The system further includes one or more fluid inlets and fluid outlets communicating with the fluid circulation space and a pump connectable to the fluid outlets. The pump is operable to circulate a thermal exchange fluid (e.g., a liquid such as water or an isotonic solution that inhibits the transfer of ions from the tissue) through the fluid circulation space under negative or nearly negative gauge pressure. For example, the pump normally circulates the thermal exchange fluid through the fluid circulation space at a gauge pressure between about positive 0.1 and about negative 10 pounds per square inch as measured at a fluid outlet.

Additionally, the system may further include a thermal exchange fluid reservoir connectable with the fluid inlets to supply thermal exchange fluid to the system. Thus, in practice the pump will draw thermal exchange fluid from the reservoir through the fluid inlet and into the fluid circulation space, allowing the thermal exchange fluid to directly contact the tissue region of interest. To heat the tissue region of interest, the thermal exchange fluid should be capable of releasing heat to the tissue region of interest. To cool the tissue region of interest, the thermal exchange fluid should be capable of absorbing heat from the tissue region of interest.

According to yet another aspect of the present invention, a method for local exchange of thermal energy with a tissue region of interest includes the step of covering the tissue region of interest with a flexible membrane to define a fluid circulation space between the tissue region of interest and the interior side of the flexible membrane. The method further includes the steps of interconnecting a fluid inlet to the fluid circulation space with a reservoir for fluid flow therebetween and coupling a fluid outlet from the fluid circulation space with a pump for fluid flow therebetween. The pump is operated to draw thermal exchange fluid from the reservoir through the fluid circulation space for heat transfer between the fluid and the tissue region of interest. In this regard, the fluid may be drawn by the pump through the fluid circulation space at negative or nearly negative gauge pressure (e.g., between about 0.1 psi and about −10.0 psi). The efficiency of the heat transfer may be further optimized by drawing the thermal exchange fluid through the fluid circulation space at a high flow rate. For example, the thermal exchange fluid may be circulated at a flow rate of between about 0.3 liters and about 4 liters per each minute for each square-meter of surface area covered by the flexible membrane (i.e. between about 0.3 liters/min-m$^2$ and about 4 liters/min-m$^2$).

The method may also include the step of sealing a periphery of the flexible membrane to a periphery of the tissue region of interest. In this regard, a sealable edge on the periphery of the flexible membrane is positionable on the periphery of the tissue region of interest. When the pump is operated, negative or nearly negative gauge pressure is supplied to facilitate establishment of a sealed arrangement. The sealing step may also include utilizing an adhesive to aid in sealing a periphery of the flexible membrane to the periphery of the tissue region of interest or using a non-soluble, high viscosity gel to aid in sealing the periphery of the flexible membrane to the periphery of the tissue region of interest. To take advantage of the negative or nearly negative pressure and to maintain the seal between the periphery of the flexible membrane and the periphery of the tissue region of interest when the pump is not operated, the method may further include the step of maintaining the reservoir of thermal exchange fluid at a lower height than the tissue region of interest According to a further aspect of the present invention, an apparatus for local exchange of thermal energy with a tissue region of interest includes a flexible membrane configured for covering the tissue region of interest. The apparatus also includes a spacing structure for maintaining an interior side of the flexible membrane in a spaced relation with the tissue region of interest thereby defining a fluid circulation space between the interior side of the flexible membrane and the tissue region of interest. At least one fluid inlet communicating with the fluid circulation space and at least one fluid outlet communicating with the fluid circulation space are provided through the flexible membrane. The apparatus further includes a sealable edge configured to provide a seal between a periphery of the flexible membrane and a periphery of the tissue region of interest. A thermal exchange fluid is circulatable through the fluid circulation space from the fluid inlet(s) to the fluid outlet(s) at a predetermined gauge pressure which does not break the seal between the periphery of the flexible membrane and the periphery of the tissue region of interest. In this regard, the thermal exchange fluid may be circulated at a negative or nearly negative gauge pressure (e.g., between about 0.1 psi and −10.0 psi).

According to one more aspect of the present invention, a method for local exchange of thermal energy with a tissue region of interest includes the step of covering the tissue region of interest with a flexible membrane to define a fluid circulation space between the tissue region of interest and an interior side of the flexible membrane. A seal between a sealable edge of the flexible membrane and the periphery of the tissue region of interest is then established by achieving a predetermined gauge pressure within the fluid circulation space (e.g., between about 0.1 psi and −10.0 psi). A thermal exchange fluid is then circulated through the fluid circulation space in direct contact with the tissue region of interest for exchanging thermal energy therewith. The thermal exchange fluid is circulated through fluid circulation space at the predetermined gauge pressure to maintain the seal between the sealable edge and the periphery of the tissue region of interest.

These and other aspects of the present invention should become apparent from a review of the following detailed description when taken in conjunction with the accompanying figures.

DETAILED DESCRIPTION

In the drawings, like reference numerals refer to corresponding structure throughout the views.

The present invention generally relates to a method and apparatus for heat transfer to a tissue region of interest. In practice a membrane configured for covering a tissue region of interest is positioned on the tissue region of interest. A spacing structure, disposable between an interior side of the flexible membrane and the tissue region of interest, maintains the flexible membrane in spaced relation with the tissue region of interest to define a fluid circulation space for fluid flow therebetween. Thermal exchange fluid is then drawn through the fluid circulation space and over the tissue region of interest. This results in the cooling/heating of the tissue region of interest. As a setting for the following discussion, embodiments of the invention will be described that are configured for thermal exchange with a patient's head and a patient's thigh. However, the invention may also be specifically configured for application on any body part or surface, for example a patient's torso, chest, back, neck, feet, or arm. Additionally, the invention will be described using a flexible membrane, however, it should be noted that thermal exchange hoods or pads may also be constructed from materials that are rigid or inelastic. Also, the thermal exchange fluid should comprise a fluid that is capable of at least one of absorbing heat from the tissue region of interest and releasing heat to the tissue region of interest.

Figure 1:
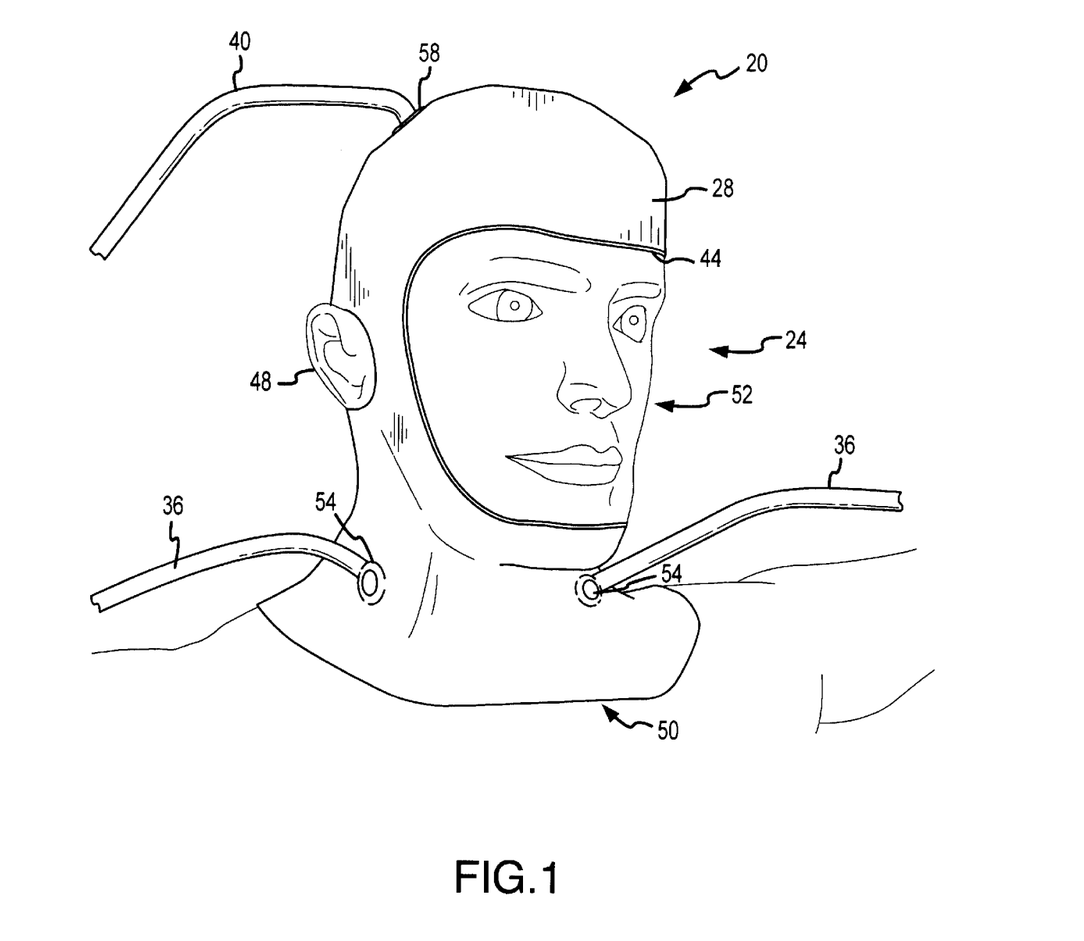
FIG. 1 is a plan view of one embodiment of an apparatus for local exchange of thermal energy with a tissue region of interest in accordance with the invention.
Figure 2:
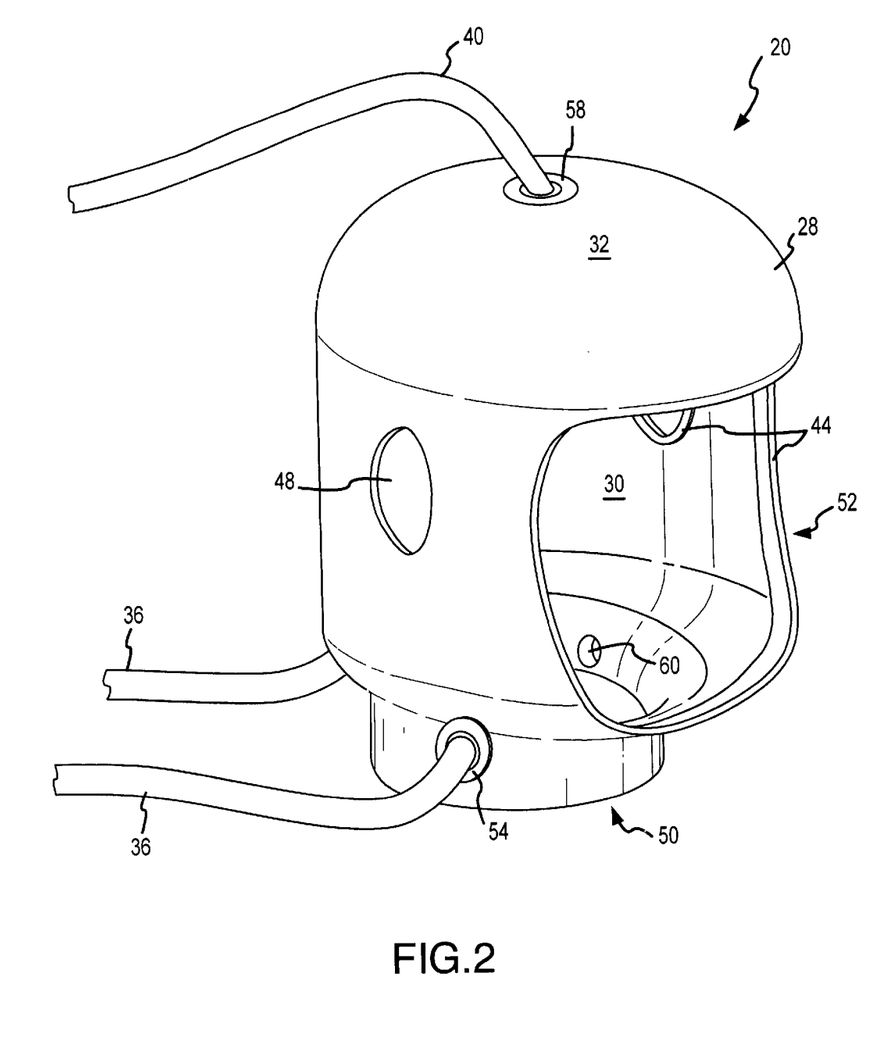
FIG. 2 is a perspective view of the embodiment shown in FIG. 1.

Referring now to FIGS. 1 and 2, there is shown an illustration of a thermal exchange hood 20. In this embodiment of the invention, the tissue region of interest 24 is a patient's head. The thermal exchange hood 20 is constructed from a flexible membrane 28 and is positioned around the tissue region of interest 24 such that the interior surface 30 of flexible membrane 28 and the tissue region of interest 24 define a fluid circulation space 34 for fluid flow therebetween. The geometry and material of the hood 20 is dictated by the need to be elastic enough to be easy to install and to provide a light positive tension to the surface of the skin to aid in positive initial sealing of the edges. Thus, the flexible membrane 28 may be comprised of latex, silicon rubber, natural rubber, a thermoplastic polyurethane, an elastomer or any variety of elastic non-porous flexible materials. The flexible membrane 28 should be conformable to the contours of the tissue region of interest 24, either with or without the application of less than ambient pressure to inhibit the existence of insulating pockets between the flexible membrane 28 and the tissue region of interest 24. Also, to minimize thermal exchange between the thermal exchange fluid and the surrounding air and thereby increase the thermal exchange efficiency, the flexible membrane 28 should be of a type that insulates the exterior 32 of the flexible membrane 28 from the fluid circulation space 34.

The hood 20 generally includes two inlet manifolds 54 and an outlet manifold 58 that overlie inlet ports 60 and an outlet port 64, respectfully. The inlet ports 60 and outlet port 64 permit thermal exchange fluid to flow into and out of the fluid circulation space 34. As shown, the outlet manifold 58 is positioned towards the top of the patient's head, while the inlet manifolds 54 are positioned towards the patient's neck. However, it should be noted that the placement and number of the inlet and outlet manifolds 54, 58 are merely illustrative and not intended to be limiting. The apparatus will work with one or more inlets and one or more outlets placed in numerous positions. A pair of inlet hoses 36 connect to the inlet manifolds 54 for transfer of thermal exchange fluid to the fluid circulation space 34. An outlet hose 40 connects to the outlet manifold 58 for transporting the thermal exchange fluid away from the fluid circulation space 34.

Figure 9:
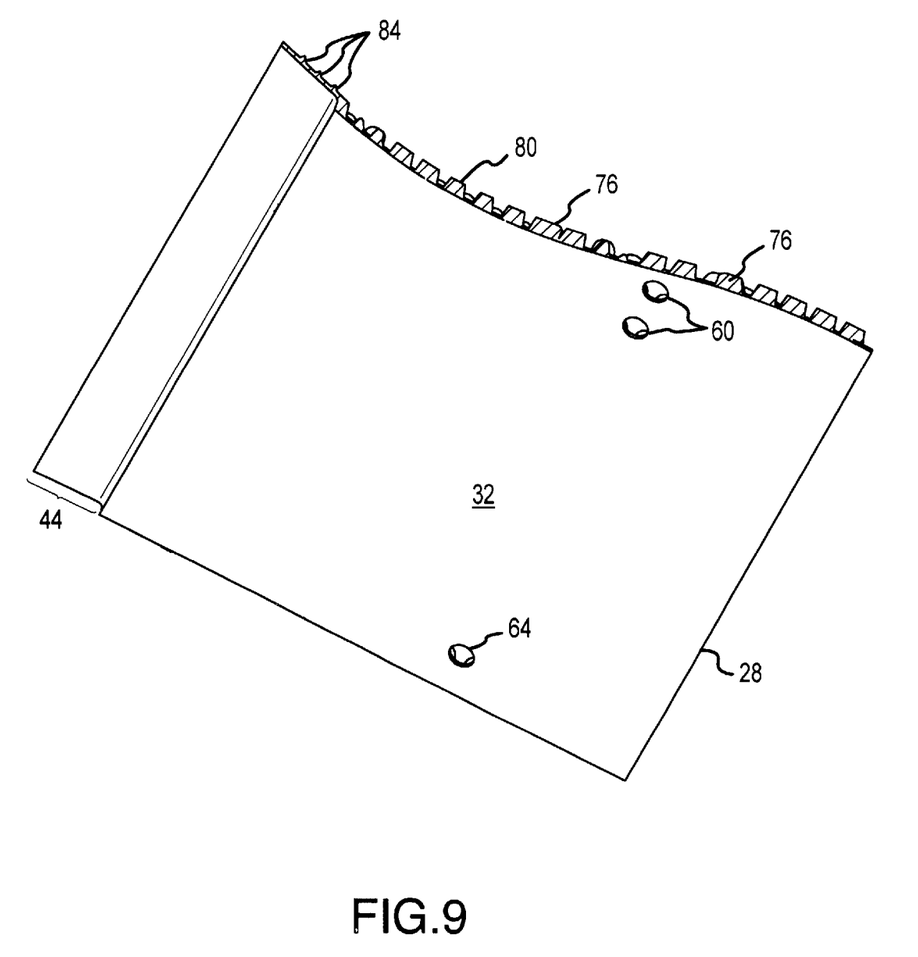
FIG. 9 is a perspective view of the exterior surface of a portion of the flexible membrane of FIG. 4.
Figure 10:
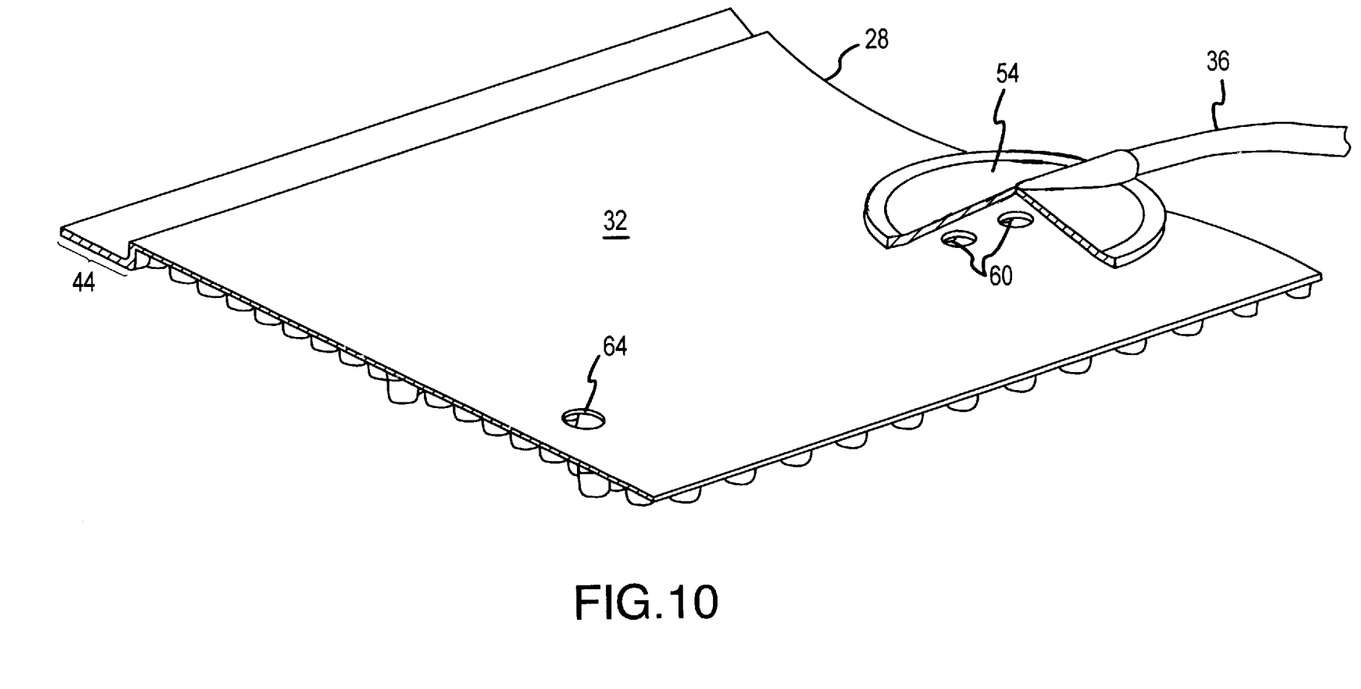
FIG. 10 is a perspective view of the exterior surface of the flexible membrane of FIG. 4 having a cut-away view of a manifold.

Referring now to FIGS. 9 and 10, there is shown perspective views of a portion of the exterior 32 of the flexible membrane 28, illustrating the attachment of an inlet or outlet manifold 54 or 58 to the exterior 32 of the flexible membrane 28. FIG. 10 shows the exterior 32 of the flexible membrane 28 of FIG. 9 with a cut-away view of the inlet manifold 54. As can be appreciated, the inlet manifold 54 and the outlet manifold 58 may be constructed in a similar fashion and secured to the exterior 32 of the flexible membrane 28 in a similar manner. For example, the inlet and outlet manifolds 54, 58 may be constructed of plastic and bonded to the exterior of the flexible membrane using an adhesive or they may be molded into the membrane.

Referring now back to FIG. 1, the hood 20 further includes a sealable edge 44 for inhibiting leakage of the thermal exchange fluid outside the tissue region of interest 24, and for inhibiting leakage of air into the fluid circulation space 34. Referring now to FIG. 2 an ear opening 48, a face opening 52, an inlet manifold 54, an inlet port 60, and an outlet manifold 58 are additionally shown. As can be inferred, the thermal exchange fluid will enter the fluid circulation space 34 through the inlet manifolds 54 and the inlet ports 60, pass over the tissue region of interest 24 and then exit through the outlet port 64 and outlet manifold 58.

Figure 3:
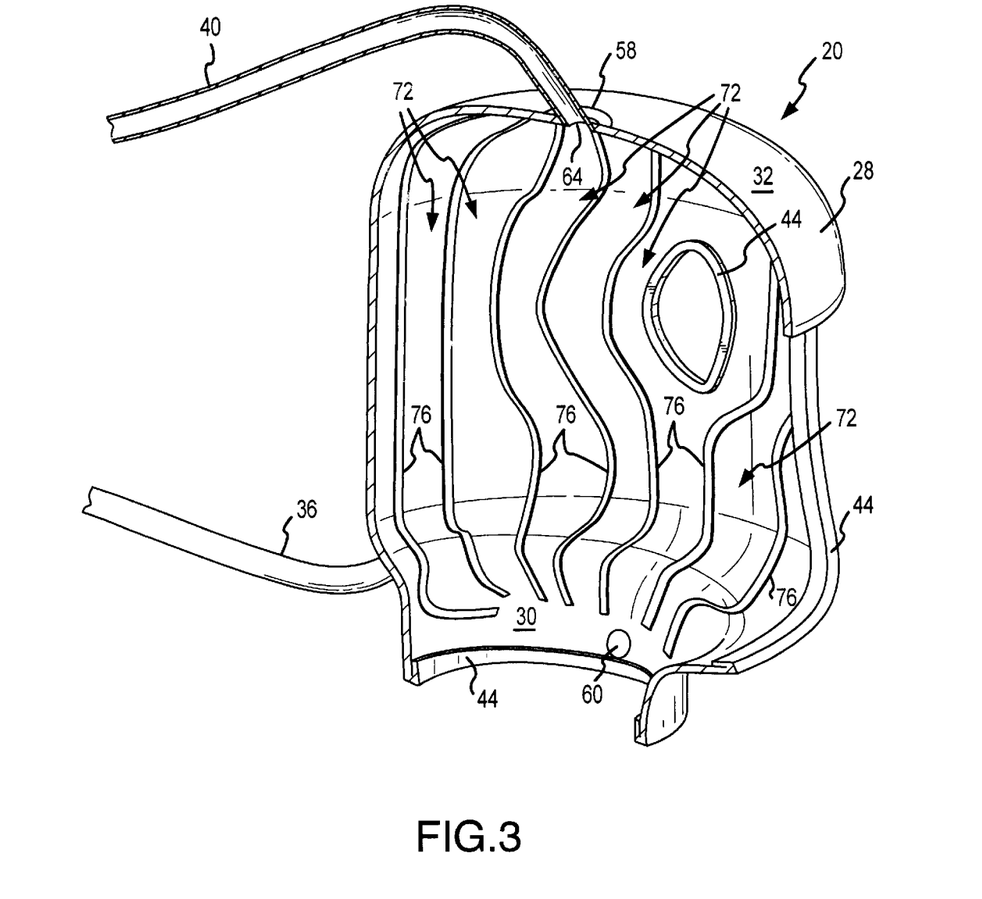
FIG. 3 is a perspective cross-sectional view of the embodiment shown in FIG. 2 taken along a centerline of the apparatus.

Referring now to the perspective cross-sectional view of FIG. 3 the hood 20 includes a spacing structure, which in this embodiment, is comprised of a plurality of ribs 76. The ribs 76 project from the interior 30 of the flexible membrane 28 to provide an air space or void between the interior 30 of the flexible membrane 28 and the tissue region of interest 24 to allow space for the thermal exchange fluid to flow from the inlet ports 60 to the outlet port 64. The number of ribs 76 used is unimportant, as long as the ribs 76 maintain at least a portion of the interior 30 of the flexible membrane 28 in a spaced relation with the tissue region of interest 24. In this regard, the ribs 76 may be about 0.25 to 1.0 inches apart and project from the interior 30 of the flexible membrane 28 by about seventy-thousandths (0.070) of an inch. Furthermore, the ribs 76 may be integrally molded to the interior 30 of the flexible membrane 28, removably attached to the interior 30 of the flexible membrane 28, or included in a net or similar structure that is disposable between the interior 30 of the flexible membrane 28 and the tissue region of interest 24. As shown, the plurality of ribs 76, interior 30 of the flexible membrane 28, and the tissue region of interest 24 define a plurality of tortuous fluid flow paths 72 from inlet ports 60 to the outlet port 64. In this regard, the fluid flow paths 72 are generally of equal length from the inlet ports 60 to the outlet port 64 in order to assure consistent fluid velocity across the entire surface of the tissue region of interest. Additionally, the fluid flow paths 72 inhibit the formation of boundary layers of stationary thermal exchange fluid that may reduce the overall efficiency of the hood 20.

There are numerous configurations to allow thermal exchange fluid to enter the fluid flow paths 72. For example, an inlet port 60 and an outlet port 64 may be associated with each fluid flow path 72. In this configuration, an inlet and an outlet port 60, 64 will be positioned between two ribs 76, thus in application, the ribs 76 will be forced next to the tissue region of interest 24 and inhibit thermal exchange fluid from flowing between fluid flow paths 72. Therefore, a specific inlet port 60 will supply thermal exchange fluid for a specific fluid flow path 72 while a specific outlet port 64 will transport thermal exchange fluid away from that fluid flow path 72. In another example, an inlet port 60 and an outlet port 64 will supply/remove thermal exchange fluid for a plurality of fluid flow paths 72. In this configuration, ribs 76 may not directly adjoin the inlet port 60 and the outlet port 64, thus one inlet port 60 may supply thermal exchange fluid to a plurality of fluid flow paths 72, while one outlet port 64 may remove thermal exchange fluid from a plurality of fluid flow paths 72.

In practice, the fluid circulation space 34 is subjected to a negative or nearly negative gauge pressure (i.e. measured relative to ambient pressure). The flexible membrane 28 conforms around the tissue region of interest 24 to provide a seal around the periphery. Thermal exchange fluid is drawn through the inlet hoses 36 through the inlet ports 60, and into the fluid circulation space 34. The thermal exchange fluid then is drawn through the fluid flow paths 72, exchanging thermal energy directly with the tissue region of interest 24. Thermal exchange fluid exits the fluid circulation space 72 through the outlet port 64. Heat transfer with the tissue region of interest 24 occurs, for example, if the thermal exchange fluid is cooler than the tissue region of interest 24. In this regard, the thermal exchange fluid will absorb heat, thereby cooling the tissue region of interest 24. Alternatively, if the thermal exchange fluid is warmer than the tissue region of interest 24, heat from the thermal exchange fluid will be absorbed, thereby warming the tissue region of interest 24. Since, the thermal exchange fluid is in direct contact with the tissue region of interest 24 the thermal resistance of the skin, hair, or other tissue is reduced allowing for greater efficiency in the heat transfer process. Additionally, thermal exchange fluid may shunt around a rib 76 or other spacing element without significantly compromising the heat transfer performance.

Figure 4:
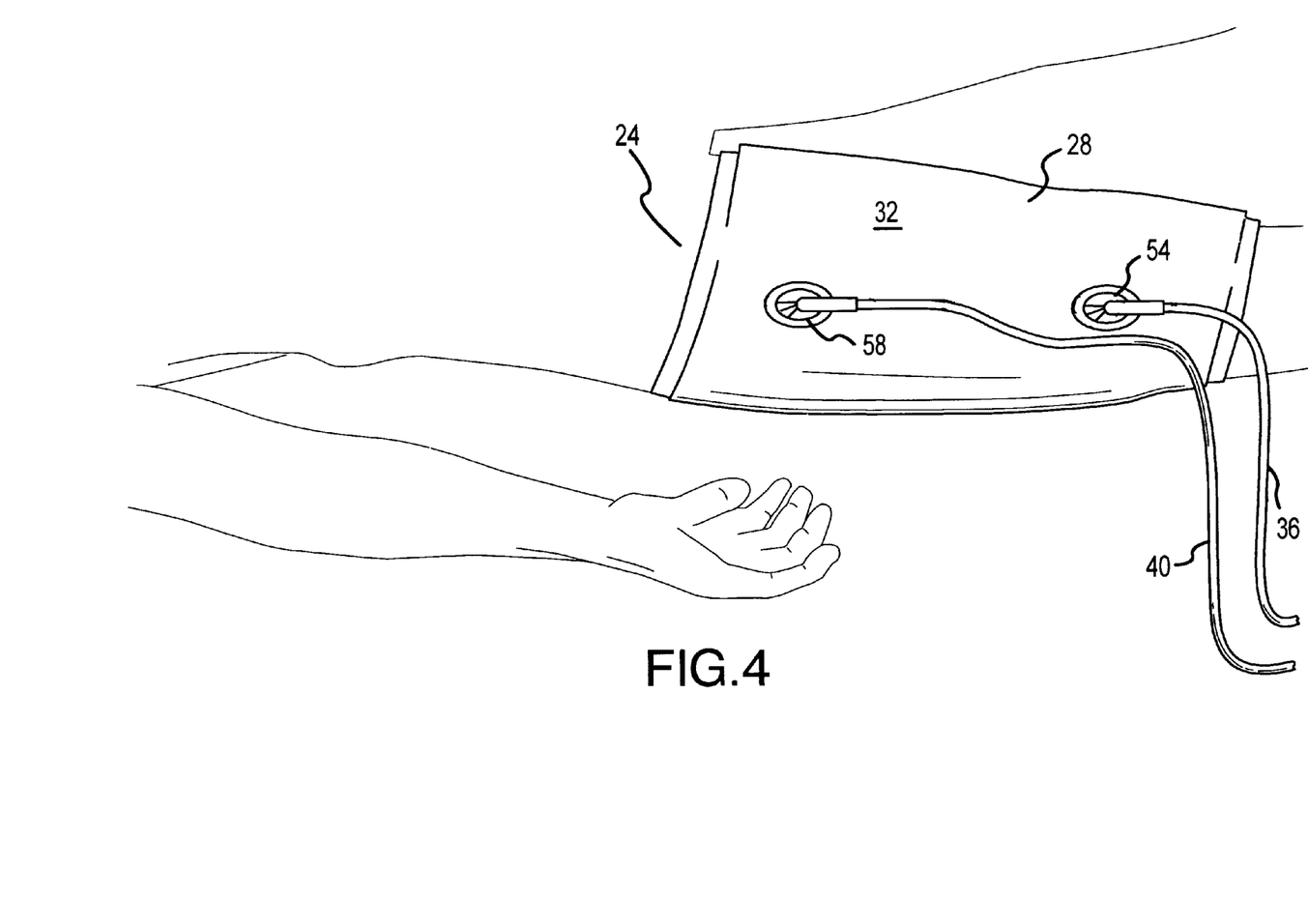
FIG. 4 is a plan view of an alternate embodiment of an apparatus for local exchange of thermal energy with a tissue region of interest in accordance with the invention.

FIG. 4 shows a plan view of an alternate embodiment of the invention in use on a patient's thigh. In this embodiment of the invention, the spacing structure, for example, a rib 76 may be configured to provide fluid flow paths 72 that spiral around the thigh from the inlet manifold 56 towards the outlet manifold 58. This maximizes the surface area of tissue region of interest 24 that the thermal exchange fluid contacts. Alternatively, the spacing structure may be configured such that the fluid flow paths 72 take a more direct approach and only define a strip on the tissue region of interest 24 to be cooled or heated.

Figure 5:
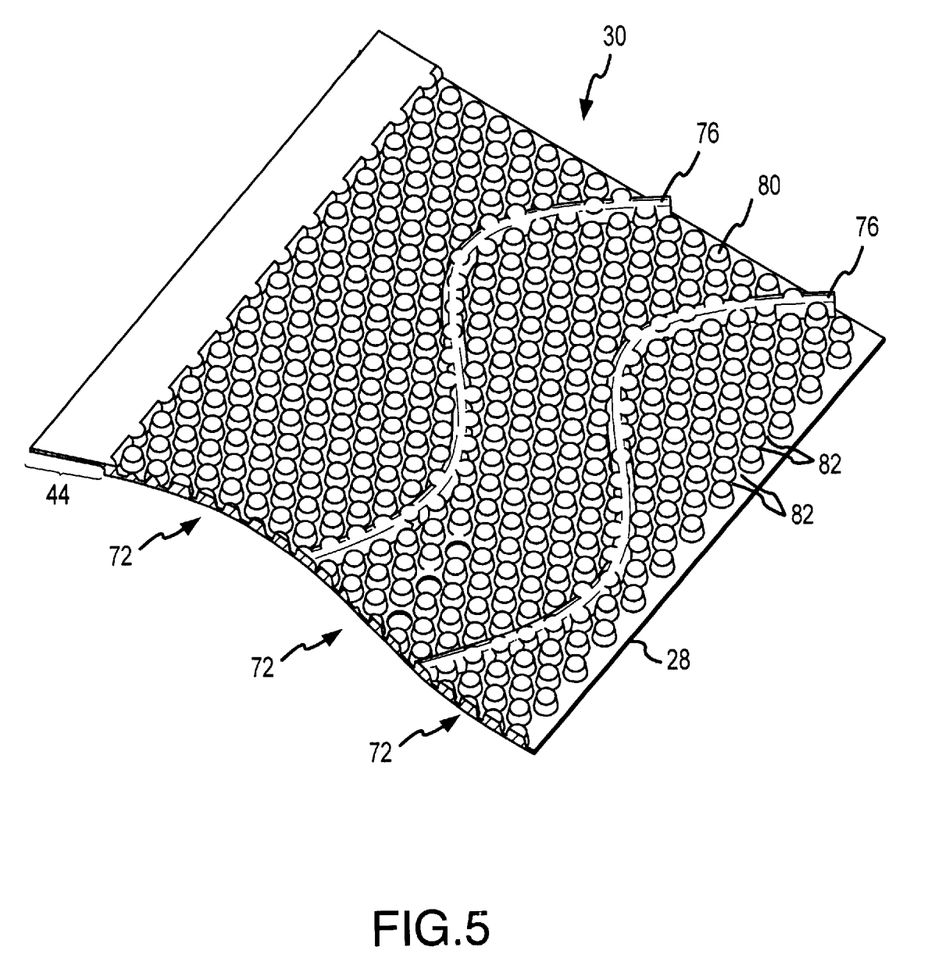
FIG. 5 is a perspective view of the interior surface of a portion of the flexible membrane of FIG. 4 having a smooth seal.

FIG. 5 shows a perspective view of the interior 30 of a portion of a flexible membrane 28 wherein the spacing structure includes both ribs 76 and studs 80. The portion of the interior 30 of the flexible membrane 28 shown includes two ribs 76, defining three fluid flow paths 72. Also, a plurality of studs 80 project from the interior 30 of the flexible membrane 28. The number, size, and type of ribs 76 shown are merely illustrative and are not meant to be limiting. As shown, the studs 80 are uniformly arrayed in rows and columns on the interior surface 30 of the flexible membrane 28 and define a plurality of interconnecting spaces 82 therebetween. The ribs 76 serpentine across the interior 30 of the flexible membrane 28 and overlap the studs 80 on occasion. In this illustrated embodiment, the studs 80 are fashioned in the form of a cylinder, but it will be appreciated that studs 80 of other than cylindrical shapes may be used in the invention. Studs 80 having hexagonal, square, rectangular or other cross-sectional shapes may be utilized. Also, the studs 80 need not be arrayed in rows and columns, since circular, random, or other arrays may function within the scope of the invention.

The interconnecting spaces 82 generally allow water, isotonic solutions or other thermal exchange fluids to flow freely therethrough, and further define a tortuous flow path within the fluid flow path 72, that further inhibits the formation of boundary layers. The studs 80 and ribs 76 are of a uniform height, approximately seventy-thousandths (0.070) of an inch, and serve to define the overall thickness of the flexible membrane 28. Additionally, the studs 80 and ribs 76 aid in maintaining the flexible membrane 28 in spaced relation with the tissue region of interest 24, and in inhibiting the collapse of the interior 30 of the flexible membrane 28 against the tissue region of interest 24. Also, the geometry and dimensions of the studs 80 and ribs 76 are such that they do not mask a significant surface area of the tissue region of interest 24. Furthermore, the crisscrossed geometry of the studs 80 and ribs 76 facilitates an even pressure drop between the inlet and outlet ports, required by a negative or nearly negative flow pressure circulating system.

Additionally, FIG. 5 shows a sealable edge 44 that is free from any spacing structure (e.g. smooth) that is approximately coplanar with the interior edges of the studs 80 and ribs 76. The sealable edge 44 is approximately 0.125 to 0.5 inches wide. Additionally, the sealable edge 44 should be positioned on a patient's skin that adjoins the periphery of the tissue region of interest, to facilitate establishment and maintenance of a sealed arrangement upon application of negative or nearly negative gauge pressures. Generally, for best results, the sealable edge 44 should be positioned next to a portion of the patient's skin that lacks substantial hair. For example, in the embodiment shown in FIG. 1, the sealable edge 44 is positioned around the neck opening 50, the ear opening 48, and the facial opening 52.

Figure 6:
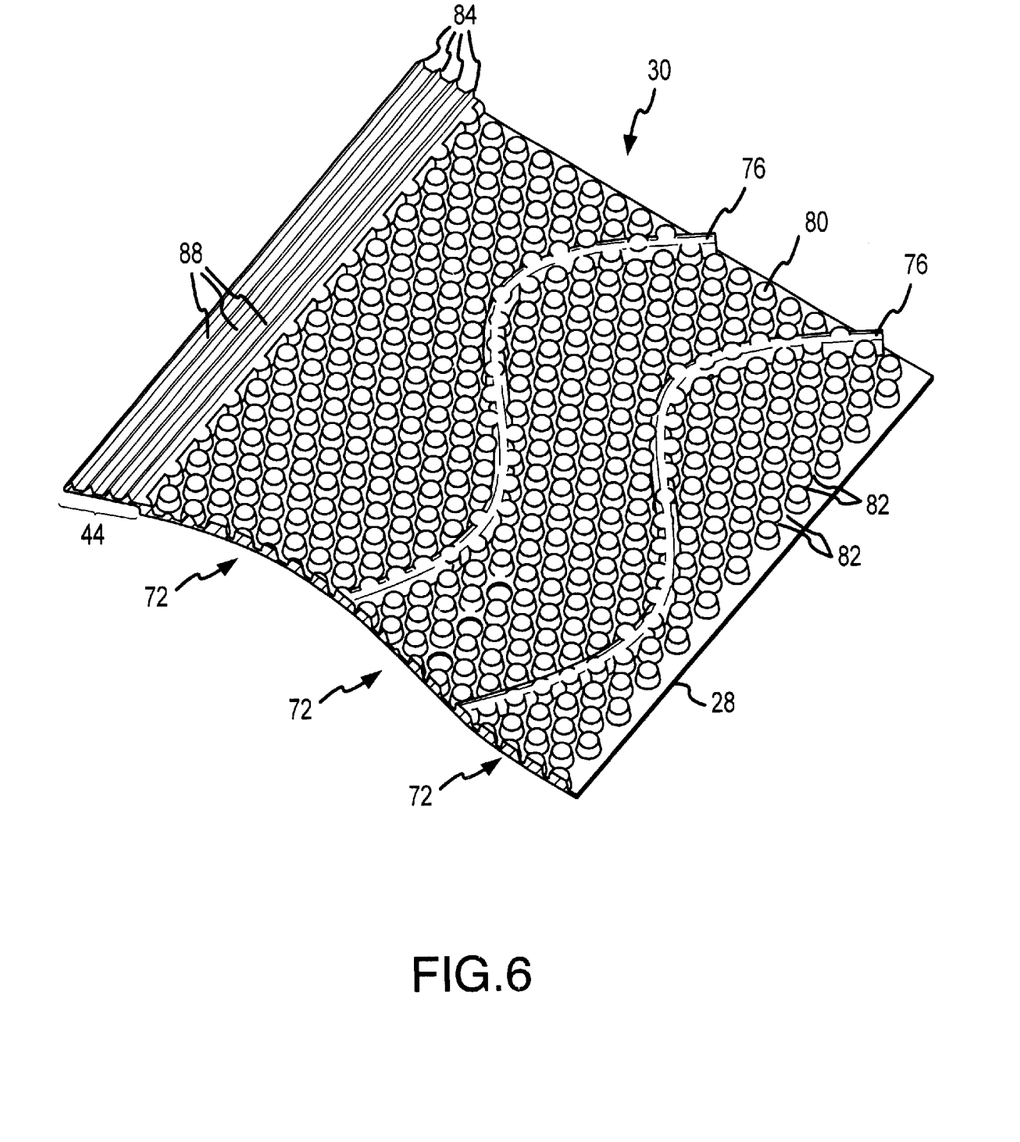
FIG. 6 is a perspective view of the interior surface of a portion of the flexible membrane of FIG. 4 having a corrugated seal.
Figure 7:
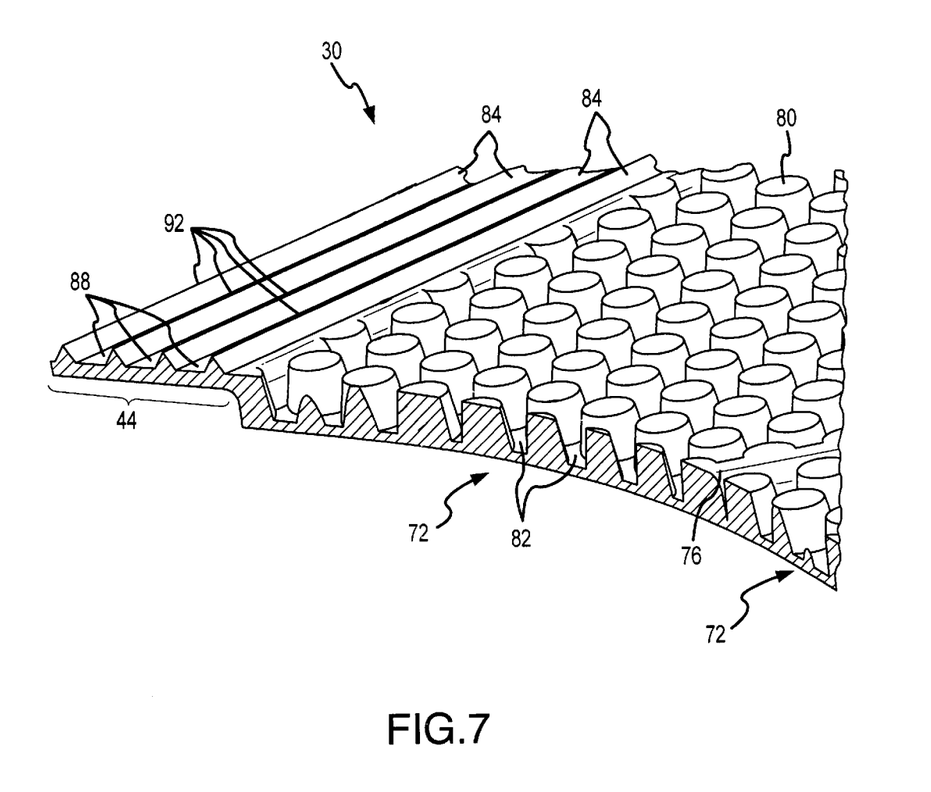
FIG. 7 is an enlarged perspective view of the portion of the flexible membrane of FIG. 6.

FIGS. 6 and 7 show an additional embodiment of the sealable edge 44 having ridges 84 and smooth sections 88. In this embodiment, the ridges 84 cooperate with the positive tension of the flexible membrane 24 to establish and maintain a sealed arrangement upon application of negative or nearly negative gauge pressure. Here, the ridges 84, project from the sealable edge 44 to define air spaces or voids therebetween, to help inhibit air leakage into the fluid flow paths 72 by concentrating a force at the apex 92 of the ridge 84, and thereby force the ridge 84 into the skin. Thus, when negative or nearly negative gauge pressure is applied, the apex 92 of the ridge 84 will deform the skin and the flat sections 88 between the ridges 84 will be approximately coplanar with the interior edges of the studs 80 and ribs 76. Negative or nearly negative gauge pressure may be established, for example, by interconnecting a pump to the outlet port 64 of the flexible membrane 24.

Figure 8:
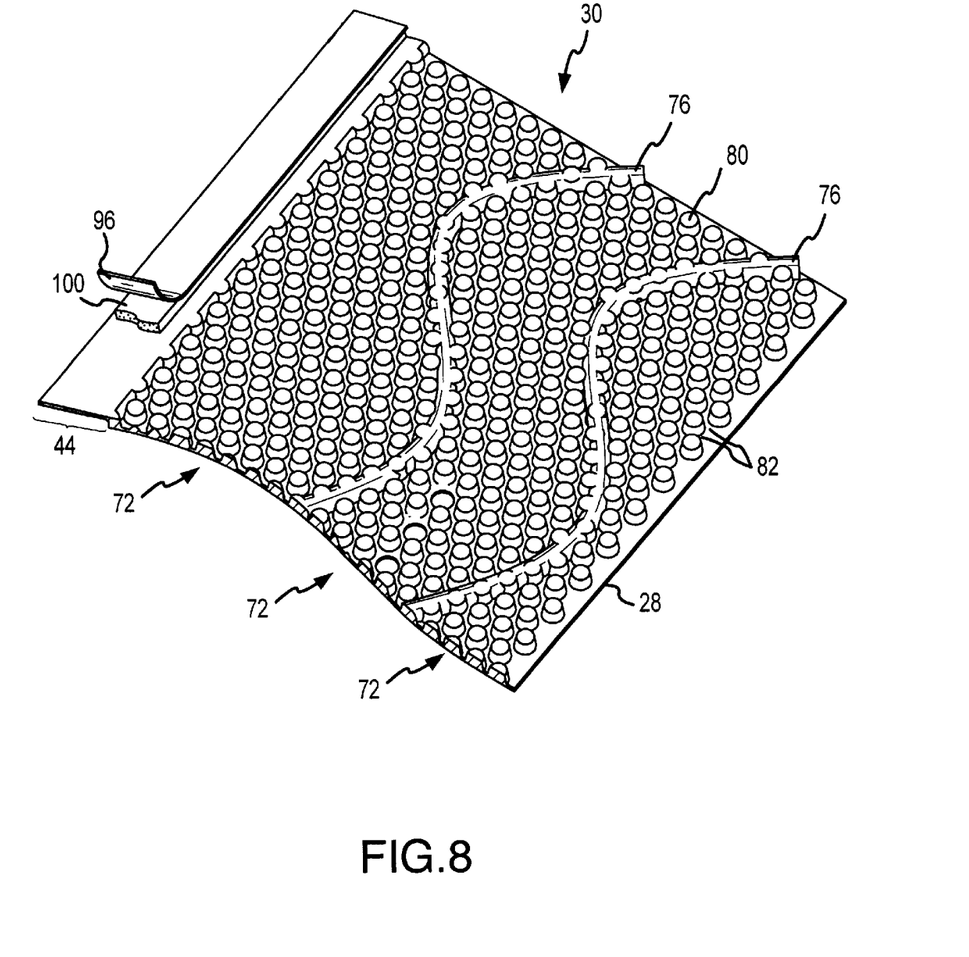
FIG. 8 is a perspective view of the interior surface of a portion of the flexible membrane of FIG. 4 having an adhesive seal.

FIG. 8 shows a third embodiment of the sealable edge 44 having an adhesive strip 100. In this embodiment, the covering strip 96 is removed exposing the adhesive strip 100 and the sealable edge 44 is affixed to the skin on the periphery of the tissue region of interest 24. The adhesive strip 100 aids in facilitating a tight seal when the fluid circulation space is subjected to negative nearly negative gauge pressure. In this regard, the adhesive strip 100 on the sealable edge 44 should be comprised of a material having sufficient adhesive strength for holding the flexible membrane 28 in place without having too great of an adhesive strength so as to cause tissue damage during removal.

The above-described embodiments of the sealable edge 44 allow for the sealable edge 44 to grip to the patient's skin, and thus helps maintain the conformance of the flexible membrane 28 to the tissue region of interest 24, limiting unintentional movement of the flexible membrane 28. The conformance of the flexible membrane 28 maximizes the surface area of the tissue region of interest 24 that is in direct contact with the thermal exchange fluid, thereby enhancing the efficiency of the heat transfer process. Also, the sealable edge 44 may provide positive tension to the periphery of the tissue region of interest 24 to inhibit excessive leakage of the thermal exchange fluid away from the tissue region of interest 24. If needed, a non-soluble high viscosity gel may be used on the sealing surface of the smooth or ridged seals to minimize leakage into and out of the fluid circulation space 34.

Figure 11:
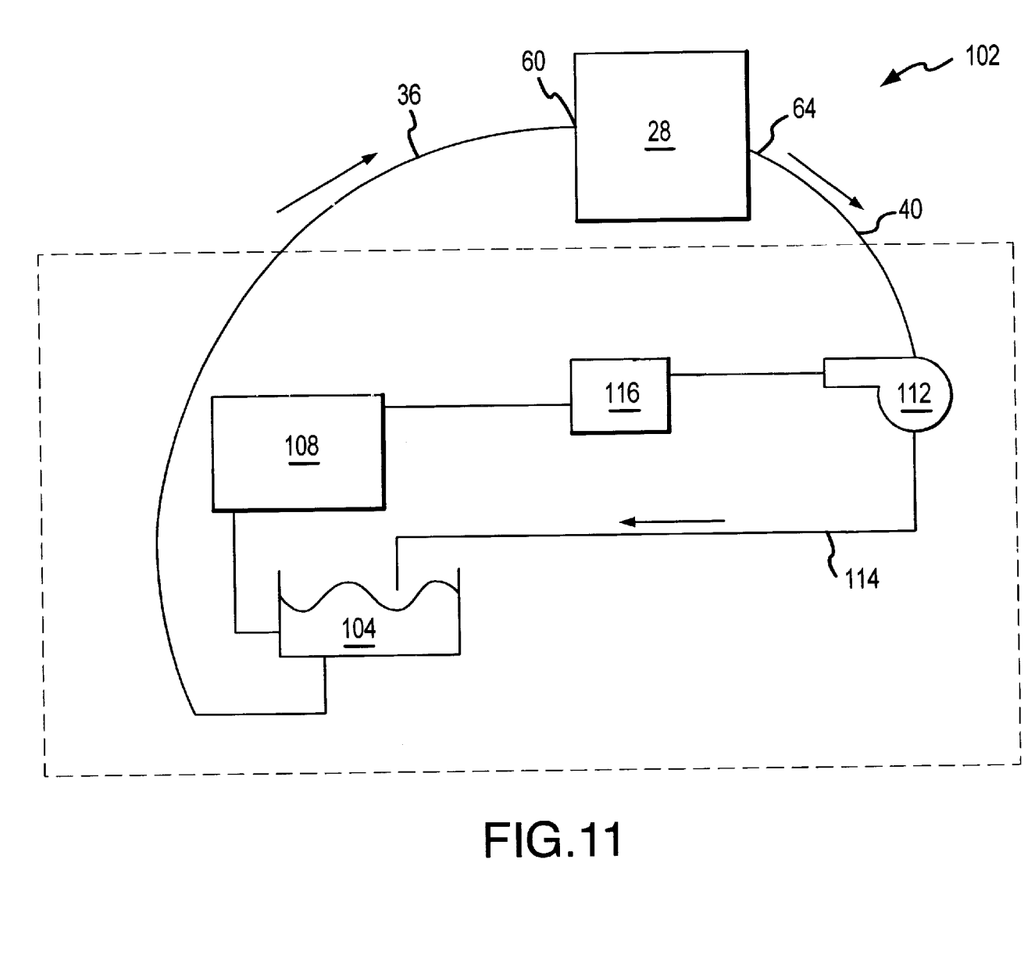
FIG. 11 is a schematic diagram of one embodiment of a thermal exchange system in accordance with the present invention.

FIG. 11 is a schematic diagram of one embodiment of a thermal exchange system 102 connected to a flexible membrane 28 such as described above. It should be appreciated that the thermal exchange system 102 may be used with hoods, such as shown in FIGS. 1–3, as well as any thermal exchange apparatus constructed in accordance with the present invention. The thermal exchange system 102 includes at least one inlet port 60 for connecting, via an inlet hose 36, a fluid reservoir 104 with the flexible membrane 28, and at least one outlet port 64 for connecting, via an outlet hose 40, a pump 112 with the flexible membrane 28. The pump 112 is of a positive displacement type capable of self-priming the system 102. Additionally, the thermal exchange system 102 may include a temperature controller 108 and a system controller 116. The inlet hose 36 connects the fluid reservoir 104 to the flexible membrane 28 to allow the thermal exchange fluid to enter the fluid circulation space 34, while the pump 112 is connected downstream, via the outlet hose 40, from the flexible membrane 28. Thus, the outlet hose 40 carries the thermal exchange fluid away from the flexible membrane 28 to the pump 112. A pump outlet line 114 carries the thermal exchange fluid away from the pump 112 and back to the fluid reservoir 104. Optionally, a temperature controller 108 that chills or heats the thermal exchange fluid may be connected to the fluid reservoir 104, and a system controller 116 may be used to control the flow rate of the thermal exchange fluid, temperature of the thermal exchange fluid, the pressure within the fluid circulation space 34, speed of the pump 112, and other system variables. The arrows on this illustration depict the thermal exchange fluid flow direction.

In practice, the pump 112 subjects the fluid circulation space 34 to negative or nearly negative gauge pressure securing the flexible membrane 28 against the tissue region of interest 24 until the spacing structures (e.g. ribs 76 and studs 80) constrain the interior 30 of the flexible membrane 30 from collapsing any further. Concurrently, the sealable edge 44 establishes a sealed arrangement on the periphery of the tissue region of interest 24 and thermal exchange fluid is drawn from the fluid reservoir 104 through the inlet hose(s) 36 and into the fluid circulation space 34. The thermal exchange fluid is drawn along the fluid flow paths 72 from the inlet port(s) 60 to the outlet port 64, directly contacting the tissue region of interest 24 before exiting the fluid circulation space 34. Generally, the gauge pressure needed to establish and maintain a sealed arrangement on the periphery of the tissue region of interest 24 is between of 0.1 psi to −10.0 psi measured at the outlet port 64. The thermal exchange fluid and/or the fluid reservoir 104 may be optionally heated or cooled by a temperature controller 108. Additionally, the fluid reservoir 104 may be located below or at the same elevation as the tissue region of interest 24, but should be no higher than the inlet port(s) 60 to prevent possible pressure from breaking the seals when the pump 112 is stopped.

The method and apparatus of the present invention allows for high heat transfer efficiency due to the thermal exchange fluid being in direct contact with the tissue region of interest 24, i.e. the thermal exchange fluid can permeate hair located on the tissue region of interest 24, thus hair will not act as an effective insulating layer. Further, a high flow rate (e.g. between about 0.5 liters/min-m$^2$ and 4.0 liters/min-m$^2$) of the thermal exchange fluid through the fluid circulation space 34 enhances the efficiency of thermal transfer. Because the apparatus is operated under negative or nearly negative gauge pressure, the sealable edge around the tissue region of interest 24 need not be perfect as small amounts of air entering the fluid circulation space 34 will not significantly reduce the thermal exchange fluid flow rate. Additionally, because of the negative or nearly negative gauge pressure system, thermal exchange fluid will not leak out into the surgical area even if the device is accidentally punctured, but instead will continue to be drawn to the outlet port 64.

The foregoing description of the invention has been presented for the purposes of illustration and description. Furthermore, the descriptions are not intended to limit the invention to the form disclosed herein. Consequently, variations and modifications commensurate with the above teachings, skill, and knowledge of the relevant art are within the scope of the invention. The embodiments described hereinabove are further intended to explain best modes known of practicing the invention and to enable others skilled in the art to utilize the invention in such, or other embodiments and with various modifications required by the particular application(s) or use(s) of the invention. It is intended that the appended claims be construed to include alternative embodiments to the extent permitted by the prior art.

What is claimed is:

1. An apparatus for local exchange of thermal energy with a tissue region of interest, said apparatus comprising:

a flexible membrane configured for covering said tissue region of interest, said flexible membrane having an exterior side and an interior side;

a spacing structure for maintaining said interior side in a spaced relation with said tissue region of interest, wherein a fluid circulation space is defined between said interior side and said tissue region of interest;

at least one fluid inlet communicating with said fluid circulation space; and at least one fluid outlet communicating with said fluid circulation space, wherein a thermal exchange fluid is circulatable through said fluid circulation space from said at least one fluid inlet to said at least one fluid outlet at a gauge pressure no greater than 0.1 psi.

2. The apparatus of claim 1 wherein said gauge pressure is negative.

3. The apparatus of claim 2 wherein said gauge pressure is no less than −10.0 psi.

4. The apparatus of claim 1 wherein said flexible membrane comprises an elastic material.

5. The apparatus of claim 4 wherein said elastic material comprises one of a silicone rubber, a natural rubber, an elastomer, a thermoplastic polyurethane, and a latex material.

6. The apparatus of claim 1 wherein said flexible membrane further comprises a sealable edge configured to provide a seal between a periphery of said flexible membrane and a periphery of said tissue region of interest.

7. The apparatus of claim 1 wherein said spacing structure comprises at least one rib projecting from said interior side of said flexible membrane.

8. The apparatus of claim 1 wherein said spacing structure comprises at least one stud projecting from said interior side of said flexible membrane.

9. The apparatus of claim 1 wherein said spacing structure comprises a net disposable between said interior side of said flexible membrane and said tissue region of interest.

10. The apparatus of claim 1 wherein said spacing structure comprises a plurality of ribs and a plurality of studs projecting from said interior side of said flexible membrane.

11. The apparatus of claim 10 wherein said studs have one of a circular, elliptical, rectangular, triangular, and hexagonal cross-section.

12. The apparatus of claim 10 wherein said studs are uniformly arrayed on said interior side of said flexible membrane.

13. The apparatus of claim 10 wherein said ribs are spaced between 0.25 inch and 1 inch apart.

14. The apparatus of claim 10 wherein said ribs and said studs are the same height.

15. The apparatus of claim 1 wherein said spacing structure defines a plurality of fluid flow paths through said fluid circulation space.

16. The apparatus of claim 15 wherein said fluid flow paths are of equal length.

17. A system for local exchange of thermal energy with a tissue region of interest, said system comprising:
    a flexible membrane configured for covering said tissue region of interest, said flexible membrane having an exterior side and an interior side;
    a spacing structure for maintaining said interior side of said flexible membrane in a spaced relation with said tissue region of interest, wherein said interior side and said tissue region of interest define a fluid circulation space therebetween;
    at least one fluid inlet communicating with said fluid circulation space;
    at least one fluid outlet communicating with said fluid circulation space, wherein a thermal exchange fluid is circulatable through said fluid circulation space from said at least one fluid inlet to said at least one fluid outlet; and
    a pump connectable to said at least one fluid outlet, wherein said pump is operable to circulate the thermal exchange fluid through said fluid circulation space at a gauge pressure no greater than 0.1 psi.

18. The system of claim 17 wherein said pump is operable to circulate the thermal exchange fluid through said fluid circulation space at a negative gauge pressure.

19. The system of claim 18 wherein said pump is operable to circulate the thermal exchange fluid through said fluid circulation space at a gauge pressure no less than −10.0 psi.

20. The system of claim 17 further comprising a thermal exchange fluid reservoir connectable with said at least one fluid inlet.

21. The system of claim 20 wherein said thermal exchange fluid reservoir is positionable at a lower height than said tissue region of interest.

22. The system of claim 17 wherein said thermal exchange fluid is capable of at least one of absorbing heat from said tissue region of interest and releasing heat to said tissue region of interest.

23. The system of claim 22 wherein the thermal exchange fluid comprises a liquid.

24. The system of claim 23 wherein the thermal exchange fluid comprises one of water and an isotonic solution.

25. A method for local exchange of thermal energy with a tissue region of interest, said method comprising the steps of:
    covering a tissue region of interest with a flexible membrane, wherein the tissue region of interest and an interior side of the flexible membrane define a fluid circulation space therebetween;
    interconnecting a fluid inlet to the fluid circulation space with a reservoir for fluid flow therebetween, the reservoir containing a thermal exchange fluid;
    coupling a fluid outlet from the fluid circulation space with a pump for fluid flow therebetween; and
    operating the pump to draw thermal exchange fluid from the reservoir through the fluid inlet into the fluid circulation space and out through the fluid outlet, wherein the thermal exchange fluid directly contacts the tissue region of interest for exchanging thermal energy therewith.

26. The method of claim 25 wherein the thermal exchange fluid is drawn through the fluid circulation space at a gauge pressure no greater than 0.1 psi.

27. The method of claim 26 wherein the thermal exchange fluid is drawn through the fluid circulation space at a negative gauge pressure.

28. The method of claim 27 wherein the thermal exchange fluid is drawn through the fluid circulation space at a gauge pressure no less than −10.0 psi.

29. The method of claim 25 further comprising the step of:
    maintaining the reservoir of thermal exchange fluid at a lower height than the tissue region of interest.

30. The method of claim 25 further comprising the step of:
    sealing a periphery of the flexible membrane to a periphery of the tissue region of interest.

31. The method of claim 30 wherein said step of sealing includes the step of utilizing an adhesive to aid in sealing the periphery of the flexible membrane to the periphery of the tissue region of interest.

32. The method of claim 30 wherein said step of sealing includes the step of using a non-soluble, high viscosity gel to aid in sealing the periphery of the flexible membrane to the periphery of the tissue region of interest.

33. The method of claim 25 wherein the thermal exchange fluid is drawn through the fluid circulation space by the pump at a flow rate in the range of 0.3 liters/min-m$^2$ to 4.0 liters/min-m$^2$.

34. The method of claim 25 further comprising the step of:
  disposing a spacing structure between the flexible membrane and the tissue region of interest.

35. An apparatus for local exchange of thermal energy with a tissue region of interest, said apparatus comprising:
  a flexible membrane configured for covering said tissue region of interest, said flexible membrane having an exterior side and an interior side;
  a spacing structure for maintaining said interior side in a spaced relation with said tissue region of interest, wherein a fluid circulation space is defined between said interior side and said tissue region of interest;
  a sealable edge configured to provide a seal between a periphery of said flexible membrane and a periphery of said tissue region of interest;
  at least one fluid inlet communicating with said fluid circulation space; and
  at least one fluid outlet communicating with said fluid circulation space, wherein a thermal exchange fluid is circulatable through said fluid circulation space from said at least one fluid inlet to said at least one fluid outlet at a predetermined gauge pressure insufficient to break the seal between said periphery of said flexible membrane and said periphery of said tissue region of interest.

36. The apparatus of claim 35 wherein said predetermined gauge pressure is no greater than 0.1 psi.

37. The apparatus of claim 36 wherein said predetermined gauge pressure is negative.

38. The apparatus of claim 37 wherein said predetermined gauge pressure is no less than −10.0 psi.

39. The apparatus of claim 35 wherein said sealable edge comprises a strip on said interior side of said flexible membrane free of any portion of said spacing structure.

40. The apparatus of claim 39 wherein an interior side of said strip is smooth.

41. The apparatus of claim 39 wherein said strip is between 0.125 to 0.5 inches wide.

42. The apparatus of claim 39 wherein said sealable edge further comprises a plurality of elongated parallel ridges projecting from an interior side of said strip.

43. The apparatus of claim 39 wherein said sealable edge further comprises an adhesive material disposed on an interior side of said strip.

44. A method for local exchange of thermal energy with a tissue region of interest, said method comprising the steps of:
  covering a tissue region of interest with a flexible membrane, wherein the tissue region of interest and an interior side of the flexible membrane define a fluid circulation space therebetween;
  establishing a seal between a sealable edge of the flexible membrane and the periphery of the tissue region of interest by achieving a predetermined gauge pressure within the fluid circulation space; and
  circulating a thermal exchange fluid through the fluid circulation space in direct contact with the tissue region of interest for exchanging thermal energy therewith, wherein the thermal exchange fluid is circulated through the fluid circulation space at the predetermined gauge pressure to maintain the seal between the sealable edge and the periphery of the tissue region of interest.

45. The method of claim 44 wherein the predetermined gauge pressure is no greater than 0.1 psi.

46. The method of claim 45 wherein the predetermined gauge pressure is negative.

47. The method of claim 46 wherein the predetermined gauge pressure is no less than −10.0 psi.

* * * * *